United States Patent [19]

Kimura et al.

[11] Patent Number: 4,777,309

[45] Date of Patent: Oct. 11, 1988

[54] CONTINUOUS PROCESS FOR PRODUCING 5-VINYL-2-NORBORNENE

[75] Inventors: Kazuo Kimura, Ichihara; Masahiro Usui; Fujio Masuko, both of Chiba, all of Japan

[73] Assignee: Sumitomo Chemical Company, Limited, Osaka, Japan

[21] Appl. No.: 104,516

[22] Filed: Sep. 29, 1987

Related U.S. Application Data

[63] Continuation-in-part of Ser. No. 941,422, Dec. 15, 1986, abandoned.

[30] Foreign Application Priority Data

Jan. 18, 1986 [JP] Japan .................................. 61-8603

[51] Int. Cl.$^4$ ............................................... C07C 3/00
[52] U.S. Cl. .................................... 585/361; 585/364; 585/366
[58] Field of Search ..................... 585/361, 366, 363

[56] References Cited

U.S. PATENT DOCUMENTS 4,538,013  8/1985  Donike et al. ........................ 526/83

FOREIGN PATENT DOCUMENTS 2113246  11/1971  Fed. Rep. of Germany .
94175  12/1972  Fed. Rep. of Germany .
3311405  3/1983  Fed. Rep. of Germany ...... 585/361
3307486  9/1984  Fed. Rep. of Germany .
4025941  11/1970  Japan .................................. 585/361
9164731  3/1983  Japan .................................. 585/361
7302865  3/1973  Netherlands ........................ 585/361
332069  6/1970  U.S.S.R. ............................. 585/361
0462810  3/1973  U.S.S.R. ............................. 585/361

*Primary Examiner*—Asok Pal
*Attorney, Agent, or Firm*—Stevens, Davis, Miller & Mosher

[57] ABSTRACT

A continuous process for producing 5-vinyl-2-norbornene, useful as the raw material of 5-ethylidene-2-norbornene used as a termonomer for EPDM, from a mixture of cyclopentadiene and butadiene or from a mixture of cyclopentadiene and dicyclopentadiene and butadiene by the Diels-Alder reaction which process comprises adding from 10 to 10,000 ppm of N,N-diethylhydroxylamine or 4-oxo-2,2,6,6-tetramethylpiperidine-1-oxyl relative to the total weight of cyclopentadiene and butadiene or of a mixture of cyclopentadiene and dicyclopentadiene and butadiene, continuously introducing the resulting mixture into a pressure reaction vessel, allowing them to react in the absence of any gas phase portion within the said pressure reaction vessel, and continuously withdrawing the reaction product.

8 Claims, No Drawings

CONTINUOUS PROCESS FOR PRODUCING 5-VINYL-2-NORBORNENE

This application is a continuation-in-part of application Ser. No. 941,422, filed Dec. 15, 1986, now abandoned.

This invention relates to a continuous process for producing 5-vinyl-2-norbornene which comprises continuously introducing cyclopentadiene and 1,3-butadiene or a mixture of cyclopentadiene and dicyclopentadiene and 1,3-butadiene in the presence of N,N-diethylhydroxylamine or 4-oxo-2,2,6,6-tetramethylpiperidine-1-oxyl into a pressure reaction vessel, allowing them to react in the absence of any gas phase portion within said pressure reaction vessel, and continuously withdrawing the reaction product. As used herein, pressure reaction vessel means an autoclave equipped with a stirrer. 5-Vinyl-2-norbornene is very useful as the raw material of 5-ethylidene-2-norbornene used as a termonomer for EPDM.

The Diels-Alder reaction is characterized by the additive reaction of an olefin having an activated double bond (a dienophile) with a conjugated diene. Since the reaction proceeds thermally, it is desirable in this respect to carry out the reaction at relatively high temperature, for example at from 70° to 250° C. However, in such a high temperature reaction, cyclopentadiene and butadiene of the raw material and cyclic olefins of the reaction product are liable to polymerize, which causes such troubles as clogging of the apparatus due to the deposition and adhesion of polymer and formation of polymer film on the inner wall surface of the apparatus, making long-time continuous operation difficult in practice.

As to the means for preventing the polymerization of reactants in the Diels-Alder reaction conducted at relatively high temperature, for example British Patent No. 923,462 discloses the addition of organic cobalt compounds and U.S. Pat. No. 3,201,484 discloses the addition of organic nickel compounds. However, since these compounds are unstable in the air and hence are troublesome to handle, they are unsuitable to be used in carrying out the Diels-Alder reaction in practice. Further, Japanese Patent Application Kokoku (Post-Exam. Publn.) No. 7,131/82 discloses the use of p-phenylenediamine or the like as the polymerization inhibitor, but their effect is not satisfactory.

Another problem involved in this Diels-Alder reaction is that since both of the reactants are a diene and act as a dienophile, a large variety of reaction products are formed in the reaction. Thus, in addition to intended 5-vinyl-2-norbornene and above-mentioned polymers, there are formed 4-vinyl-1-cyclohexene, tetrahydroindene, cyclooctadiene and so forth, particularly a substantial amount of 4-vinyl-1-cyclohexene which is the dimer of butadiene, which causes to reduce the selectivity for 5-vinyl-2-norbornene.

The object of this invention is to provide a process for producing 5-vinyl-2-norbornene continuously for a long time and with good selectivity by correcting the bove-mentioned defects of prior arts, namely by preventing such troubles as clogging of the apparatus due to the deposition and adhesion of polymers and formation of polymer film on the inner wall surface of the apparatus, in the process for producing 5-vinyl-2-norbornene by the above-mentioned Diels-Alder reaction.

This invention relates to a continuous process for producing 5-vinyl-2-norbornene from cyclopentadiene and butadiene or from a mixture of cyclopentadiene and dicyclopentadiene and butadiene by the Diels-Alder reaction which process comprises adding from 10 to 10,000 ppm of N,N-diethylhydroxylamine or 4-oxo-2,2,6,6-tetramethylpiperidine-1-oxyl relative to the total weight of cyclopentadiene and butadiene or of a mixture of cyclopentadiene and dicyclopentadiene and butadiene, continuously introducing the resulting mixture into a pressure reaction vessel, allowing them to react in the absence of any gas phase portion within the said pressure reaction vessel, and continuously withdrawing the reaction product.

4-Vinyl-1-cyclohexene, a side reaction product, is formed by the dimerization of butadiene. According to the analytical study of the present inventors, when a gas phase portion is present within the pressure reaction vessel in the reaction of cyclopentadiene or a mixture of cyclopentadiene and dicyclopentadiene with butadiene, the relative concentration of butadiene, which has a higher vapor pressure, becomes high in the gas phase portion of the pressure reaction vessel, which promotes the formation of 4-vinyl-1-cyclohexene.

According to the process of this invention, cyclopentadiene or a mixture of cyclopentadiene and dicyclopentadiene and butadiene are continuously introduced into a pressure reaction vessel, allowed to react under conditions such that the vessel is filled with liquid and contains no gas phase portion, and the reaction product is continuously withdrawn, whereby the formation of 4-vinyl-1-cyclohexene can be reduced and the selectivity of 5-vinyl-2-norbornene based on butadiene can be enhanced.

Further, by continuously injecting into the pressure reaction vessel N,N-diethylhydroxylamine or 4-oxo-2,2,6,6-tetramethylpiperidine-1-oxyl as a polymerization inhibitor, polymerization in the pressure reaction vessel is suppressed and continuous operation can be carried out for a long time without the troubles of clogging of the apparatus due to deposition and adhesion of polymer and formation of polymer film on the inner wall surface of the apparatus. Also, since the polymerization of butadiene and 5-vinyl-2-norbornene is suppressed, the selectivity of 5-vinyl-2-norbornene base on butadiene can be further enhanced.

The process of this invention is carried out by injecting cyclopentadiene and butadiene or a mixture of cyclopentadiene and dicyclopentadiene and butadiene continuously by means of a metering pump or the like into a pressure reaction vessel maintained at a temperature of from about 80° to 180° C., preferably from 90° to 160° C., and at a pressure of from about 5 to 60 kg/cm², preferably from 10 to 45 kg/cm², more preferably at a reaction temperature of 90° to 150° C. and a reaction pressure not less than the sautrated vapor pressure of the reaction mixture at the reaction temperature, adding continuously thereto from 10 to 10,000 ppm, preferably from 100 to 5,000 ppm, of N,N-diethylhydroxylamine or 4-oxo-2,2,6,6-tetramethylpiperidine-1-oxyl relative to the total weight of feed materials, allowing them to react for from about 0.1 to 5 hours, preferably from about 0.3 to 2 hours, and simultaneously withdrawing the reaction product continuously.

This invention will be described further below with reference to Examples. In the Examples, the amount of polymeric byproducts was quantitatively determined by treating the reaction liquid at 92° C. under a reduced pressure of 2 mmHg, and measuring the amount of the remaining heavy matter.

EXAMPLE 1

Into a pressure vessel of 200 ml volume maintained at a temperature of 140° C. and a pressure of 40 kg/cm$^2$ were fed with a plunger pump butadiene and cyclopentadiene in a molar ratio of 1.2:1 so as to give a residence time of 35 minutes. Simultaneously, 2,500 ppm of N,N-diethylhydroxylamine was added thereto as a polymerization inhibitor. The reaction liquid was continuously withdrawn while the reaction vessel being maintained full of liquid, and was analyzed. The reaction was continuously carried out for 1000 hours. After the reaction had been stopped, no deposition of polymeric byproducts was observed in the autoclave and the inside of the vessel was clean. The concentration of polymeric byproducts in the reaction liquid was 0.04% by weight.

The results of the reaction as examined by gas chromatographic analysis were: conversion of butadiene, 21.0%; selectivity of 5-vinyl-2-norbornene based on butadiene, 67.8%; selectivity of 4-vinyl-1-cyclohexene on the same basis, 16.8%.

EXAMPLE 2

Into a pressure reaction vessel of 200 ml volume maintained at a temperature of 130° C. and a pressure of 35 kg/cm$^2$ were fed with a plunger pump butadiene and a mixture of 95% by weight of cyclopentadiene and 5% by weight of dicyclopentadiene so as to give a molar ratio of butadiene to cyclopentadiene of 1.3:1.0 and a residence time of 50 minutes. Simultaneously, 1,500 ppm of N,N-diethylhydroxylamine was added thereto as a polymerization inhibitor. The reaction liquid was continuously withdrawn while the reaction vessel being maintained full of liquid, and was analyzed. The reaction was continuuusly carried out for 500 hours. After the reaction had been stopped, no deposition of polymeric byproducts was observed in the autoclave and the inner wall of the vessel was clean. The concentration of polymeric byproducts in the reaction liquid was 0.03% by weight.

The results of the reaction as examined by gas chromatographic analysis were: conversion of butadiene, 16.7%; selectivity of 5-vinyl-2-norbornene based on butadiene, 70.1%; selectivity of 4-vinyl-1-cyclohexene on the same basis, 16.6%.

EXAMPLE 3

A reaction was carried out under the same conditions as in Example 1 except that 600 ppm of N,N-diethylhydroxylamine was added instead of 2,500 ppm. The reaction was conducted continuously for 500 hours. After stoppage of the reaction, no deposition of polymeric byproducts was observed in the autoclave and the inside of the vessel was clean. The concentration of the polymeric byproducts in the reaction liquid (at the time) was 0.17% by weight.

The results of the reaction as examined by gas chromatographic analysis were: conversion of butadiene, 21.3%; selectivity of 5-vinyl-2-norbornene based on butadiene, 67.0%; selectivity of 4-vinyl-1-cyclohexene on the same basis, 16.6%.

EXAMPLE 4

Into a pressure reaction vessel of 200 ml volume maintained at a temperature of 140° C. and a pressure of 40 kg/cm$^2$ were fed with a plunger pump butadiene and cyclopentadiene in a molar ratio of 1.2:1 so as to give a residence time of 35 minutes. Simultaneously, 2,500 ppm of 4-oxo-2,2,6,6-tetramethylpiperidine-1-oxyl was added thereto as a polymerization inhibitor. The reaction liquid was continuously withdrawn while the reaction vessel being maintained full of liquid, and was analyzed. The reaction was carried out continuously for 120 hours. After stoppage of the reaction, no deposition of polymeric byproducts was observed in the autoclave and the inside of the vessel was clean. The concentration of polymeric byproducts in the reaction liquid was 0.16% by weight. The results of the reaction as examined by gas chromatographic analysis were: conversion of butadiene, 21.3%; selectivity of 5-vinyl-2-norbornene based on butadiene, 67.1%; selectivity of 4-vinyl-1-cyclohexene on the same basis, 16.6%.

EXAMPLE 5

Into a pressure reaction vessel of 200 ml volume maintained at a temperature of 130° C. and a pressure of 35 kg/cm$^2$ were fed with a plunger pump butadiene and a mixture of 95% by weight of cyclopentadiene and 5% by weight of dicyclopentadiene so as to give a molar ratio of butadiene to cyclopentadiene of 1.3:1.0 and a residence time of 50 minutes. Simultaneously, 1,500 ppm of 4-oxo-2,2,6,6-tetramethylpiperidine-1-oxyl was added thereto as a polymerization inhibitor. The reaction liquid was continuously withdrawn while the vessel being maintained full of liquid, and as analyzed. The reaction was carried out continuously for 140 hours. After stoppage of the reaction, no deposition of polymeric byproducts was observed in the autoclave and the inside of the vessel was clean. The concentration of polymeric byproducts in the reaction liquid was 0.11% by weight. The results of the reaction as examined by gas chromatographic analysis were: conversion of butadiene, 16.9%; selectivity of 5-vinyl-2-norbornene based on butadiene, 69.6%; selectivity of 4-vinyl-1-cyclohexene on the same basis, 16.5%.

EXAMPLE 6

A reaction was carried out under the same conditions as in Example 1 except that 600 ppm of 4-oxo-2,2,6,6-tetramethylpiperidine-1-oxyl was added instead of N,N-diethylhydroxylamine. The reaction was conducted continuously for 120 hours. After stoppage of the reaction, no deposition of polymeric byproducts was observed in the autoclave and the inside of the vessel was clean. The concentration of polymeric byproducts in the reaction liquid was 0.6% by weight. The results of the reaction as examined by gas chromatographic analysis were: conversion of butadiene, 22.2%; selectivity of 5-vinyl-2-norbornene based on butadiene, 64.4%; selectivity of 4-vinyl-1-cyclohexene on the same basis, 16.0%.

COMPARATIVE EXAMPLE 1

In a pressure reaction vessel of 200 ml volume were placed 27 g of cyclopentadiene, 27 g of butadiene, and 0.2 g of N,N'-diphenyl-p-phenylenediamine, and allowed to react at 140° C. The reaction time was selected so as to give the same percentage of conversion of butadiene as in Example 1.

After completion of the reaction, polymeric byproducts were found deposited in the autoclave and the inside of the vessel was soiled. The results of the reaction as examined by gas chromatographic analysis were: conversion of butadiene, 24%; selectivity of 5-vinyl-2- norbornene based on butadiene, 43%; selectivity of 4-vinyl-1-cyclohexene on the same basis, 41%.

COMPARATIVE EXAMPLE 2

A continuous operation was carried out for 120 hours under the same conditions as in Example 1 except that no polymerization inhibitor was added. After stoppage of the reaction, it was found that the autoclave was filled with polymeric byproducts and the inside was soiled. The concentration of polymeric byproducts in the reaction liquid was 2.5% by weight.

The results of the reaction as examined by gas chromatographic analysis were: conversion of butadiene, 25%; selectivity of 5-vinyl-2-norbornene based on butadiene, 54%; selectivity of 4-vinyl-1-cyclohexene on the same basis, 17%.

In a process for producing 5-vinyl-2-norbornene from cyclopentadiene and butadiene or from a mixture of cyclopentadiene and dicyclopentadiene and butadiene by the Diels-Alder reaction, the reaction can be carried out for a long time with good selectivity and without such troubles as clogging due to the deposition and adhesion of polymer in the apparatus and formation of polymer film on the inner wall surface of the apparatus by adding from 10 to 10,000 ppm of N,N-diethylhydroxylamine or 4-oxo-2,2,6,6 tetramethylpiperidine-1-oxyl relative to the total weight of cyclopentadiene and butadiene or of a mixture of cyclopentadiene and dicyclopentadiene and butadiene, continuously introducing the resulting mixture into the pressure reaction vessel, allowing them to react in the absence of any gas phase portion within the said pressure reaction vessel, and continuously withdrawing the reaction product.

What is claimed is:

1. A continuous process for producing 5-vinyl-2-norbornene by the Diels-Alder reaction which comprises:
   (a) providing a mixture of 1,3-butadiene and cyclopentadiene or of 1,3-butadiene, cyclopentadiene and dicyclopentadiene containing 10 to 10,000 ppm of N,N-diethylhydroxylamine;
   (b) continuously introducing the mixture into a pressure reaction vessel;
   (c) reacting the 1,3-butadiene with cyclopentadiene in the pressure reaction vessel in the absence of any gas phase; and
   (d) continuously withdrawing product from the pressure reaction vessel.

2. The process according to claim 1, wherein the mixture in the pressure reaction vessel is at a temperature of 90°–150° C. and at a pressure greater than the saturated vapor pressure of the reaction mixture at the reaction temperature.

3. The process according to claim 1, wherein the pressure reaction vessel is maintained full of liquid.

4. The process according to claim 1, wherein the said mixture contains 100 to 5,000 ppm of N,N-diethylhydroxylamine.

5. A continuous process for producing 5-vinyl-2-norbornene by the Diels-Alder reaction which comprises:
   (a) providing a mixture of 1,3-butadiene and cyclopentadiene or of 1,3-butadiene, cyclopentadiene and dicyclopentadiene containing 10 to 10,000 ppm of 4-oxo-2,2,6,6-tetramethylpiperidine-1-oxyl.
   (b) continuously introducing the mixture into a pressure reaction vessel;
   (c) reacting the 1,3-butadiene with cyclopentadiene in the pressure reaction vessel in the absence of any gas phase; and
   (d) continuously withdrawing product from the pressure reaction vessel.

6. The process according to claim 5, wherein the mixture in the pressure reaction vessel is at a temperature of 90°–150° C. and at a pressure greater than the saturated vapor pressure of the reaction mixture at the reaction temperature.

7. The process according to claim 5, wherein the pressure reaction vessel is maintained full of liquid.

8. The process according to claim 5, wherein the said mixture contains 100 to 5,000 ppm of 4-oxo-2,2,6,6-tetramethylpiperidine-1-oxyl.

* * * * *